United States Patent
Wang et al.

(10) Patent No.: US 11,426,454 B2
(45) Date of Patent: Aug. 30, 2022

(54) TUBERCULOSIS VACCINE, PREPARATION METHOD THEREFOR, AND USE THEREOF

(71) Applicant: SICHUAN UNIVERSITY, Chengdu (CN)

(72) Inventors: Zhenling Wang, Chengdu (CN); Yuquan Wei, Chengdu (CN)

(73) Assignee: Sichuan University, Chengdu (CN)

( * ) Notice: Subject to any disclaimer, the term of this patent is extended or adjusted under 35 U.S.C. 154(b) by 0 days.

(21) Appl. No.: 17/051,993

(22) PCT Filed: Jul. 1, 2019

(86) PCT No.: PCT/CN2019/094201
§ 371 (c)(1),
(2) Date: Oct. 30, 2020

(87) PCT Pub. No.: WO2019/210888
PCT Pub. Date: Nov. 7, 2019

(65) Prior Publication Data
US 2021/0052714 A1    Feb. 25, 2021

(30) Foreign Application Priority Data

May 2, 2018 (CN) .......................... 201810410653.5

(51) Int. Cl.
| | | |
|---|---|---|
| *C12N 1/00* | (2006.01) | |
| *C12N 1/12* | (2006.01) | |
| *C12N 1/20* | (2006.01) | |
| *A61K 39/04* | (2006.01) | |
| *A61K 39/015* | (2006.01) | |
| *A61K 39/02* | (2006.01) | |
| *A61P 31/06* | (2006.01) | |
| *A61K 9/00* | (2006.01) | |
| *A61K 31/4409* | (2006.01) | |
| *A61K 31/496* | (2006.01) | |
| *A61K 31/7036* | (2006.01) | |
| *C12N 13/00* | (2006.01) | |
| *A61K 39/00* | (2006.01) | |

(52) U.S. Cl.
CPC .............. *A61K 39/04* (2013.01); *A61K 9/007* (2013.01); *A61K 9/0019* (2013.01); *A61K 9/0043* (2013.01); *A61K 9/0053* (2013.01); *A61K 31/4409* (2013.01); *A61K 31/496* (2013.01); *A61K 31/7036* (2013.01); *A61P 31/06* (2018.01); *C12N 1/20* (2013.01); *C12N 13/00* (2013.01); *A61K 2039/521* (2013.01); *A61K 2039/54* (2013.01); *A61K 2039/542* (2013.01); *A61K 2039/543* (2013.01); *A61K 2039/544* (2013.01)

(58) Field of Classification Search
CPC . A61K 39/04; A61K 9/0019; A61K 2039/551
USPC ........ 424/9.1, 9.2, 93.1, 234.1, 248.1, 278.1
See application file for complete search history.

(56) References Cited

FOREIGN PATENT DOCUMENTS

| | | |
|---|---|---|
| CN | 1235555 A | 11/1999 |
| CN | 1420784 A | 5/2003 |
| CN | 108743931 A | 11/2018 |
| EP | 2144626 B1 | 12/2014 |
| WO | 2018006939 A1 | 1/2018 |

OTHER PUBLICATIONS

Nishihara, H.; Lawrence, C. A.; Taplin, G. V.; Carpenter, C. M. CS Sch. Med., Univ. Calif., Los Angeles, Calif., USA So Amer Rev Resp Pis, (1963) vol. 88, No. 6, pp. 827-832. (Year: 1963).*
International Search Report for International Application No. PCT/CN2019/094201.
Written Opinion of International Search Authority for International Application No. PCT/CN2019/094201.

* cited by examiner

*Primary Examiner* — Gary B Nickol
*Assistant Examiner* — Lakia J Jackson-Tongue
(74) *Attorney, Agent, or Firm* — JCIP; Joseph G. Chu; Jeremy I. Maynard

(57) ABSTRACT

The present invention relates to the field of tuberculosis vaccines, and specifically relates to a tuberculosis vaccine, a preparation method thereof, and a use thereof. To address the problem of existing vaccines being unsuitable for patients having weak immunity, the present invention provides a preparation method for a tuberculosis vaccine: first obtaining *Mycobacterium* single cell bacteria, and using low dosage radiation to irradiate periodically the *Mycobacterium* single cell bacteria, so as to obtain the tuberculosis vaccine. The present invention completely retains all of the antigen characteristics of the bacteria, and can more rapidly stimulate stronger specific immune responses, thereby achieving effective and long-lasting immunity. The vaccine prepared using the present invention has low toxicity, is rapid-acting and safer, and can be used for the prevention and treatment of tuberculosis for people having immunodeficiency.

13 Claims, 7 Drawing Sheets

Week 6 ns of the

TUBERCULOSIS VACCINE, PREPARATION METHOD THEREFOR, AND USE THEREOF

PRIORITY APPLICATION

This application claims the priority of Chinese invention patent application 201810410653.5 titled "Tuberculosis vaccine, preparation method thereof, and use thereof" filed on May 2, 2018, which is incorporated by reference in its entirety.

FIELD OF THE INVENTION

The present invention relates to the field of tuberculosis vaccines, and specifically relates to a tuberculosis vaccine, a preparation method thereof, and a use thereof.

BACKGROUND OF THE INVENTION

Tuberculosis (TB) is a serious infectious disease worldwide. According to the 2016 WHO report, there are 10.4 million new cases of TB across the world, of which, pediatric cases account for 10%. There are 480,000 cases of multidrug-resistant tuberculosis (MDR), and 100,000 cases of rifampin-resistant tuberculosis. China suffers a heavy burden from TB. According to the WHO prediction, the tuberculosis infections and incidences in countries with heavy burden from TB have the characteristics of multidrug resistant tuberculosis (MDR-TB) and AIDS combined with tuberculosis (TB/HIV) in 2016 to 2020.

Regarding the prevention of tuberculosis, *Bacillus* Calmette-Gudrin vaccine (BCG) is currently the only method to prevent tuberculosis. However, BCG is not an ideal vaccine against tuberculosis for the following reasons: firstly, its immunogenicity is insufficient, and its protective effect against tuberculosis is 0-80%, with great difference, and it can be only used for prevention of children's serious tuberculosis (miliary tuberculosis, tuberculous meningitis), with a protection period of 5 to 10 years; secondly, BCG vaccine is ineffective for people who have been infected. It is ineffective for reducing the risk of infection and infected cases after exposure, and ineffective for adolescents and adults with tuberculosis; thirdly, BCG is live attenuated vaccine, so it cannot be used for vaccination of immunocompromised populations (for example, AIDS patients, HCV patients, patients with congenital immunodeficiency, or patients taking immunosuppressive drugs); fourthly, it has obvious adverse reactions.

In recent years, many studies on TB vaccines have been reported, but no vaccines have been marketed yet. The TB vaccines under development can be divided into the following four categories: 1) Viral vector vaccines: such as Ad5Ag85A, ChAdOx1.85A/MVA85A, MVA85A/MVA85A, TB/FLU-04L, etc.; 2) Recombinant protein/adjuvant vaccines: such as H1/H56: IC31, H4: IC31, ID93+GLA-SE, M72+ASO1E, etc.; 3) *Mycobacterium* whole-cell vaccines or extract vaccines: such as *M. vaccae*, DAR-901, VPM 1002, RUTI, etc.; 4) attenuated MTB and recombinant BCG vaccines: MTBVAC, VPM1002. Except for *M. vaccae* and *M. indicus pranii* that have entered phase III clinical trials, other vaccines are in phase I or phase II.

At present, there are no TB vaccines that can work well on both adults and children, especially for immunocompromised patients; therefore, it is urgent to develop a more effective and safer TB vaccine.

SUMMARY OF THE INVENTION

An object of the present invention is to alleviate the problems of existing TB vaccines that are only effective to children but ineffective to adults, or not suitable for immunocompromised patients.

To achieve the object, the present invention provides a tuberculosis vaccine, a preparation method thereof, and a use thereof.

A preparation method for tuberculosis vaccine, comprising the following steps:

first obtaining *Mycobacterium* single cell bacteria, and using radiation at low dosage to irradiate uniformly and periodically the *Mycobacterium* single cell bacteria, to prepare the tuberculosis vaccine.

Further, the preparation method for tuberculosis vaccine, comprising the following steps:
a. obtaining *Mycobacterium* strains,
b. inoculating and culturing to logarithm growth phase,
c. adding resuspension medium, homogenizing, and sieving, and
d. obtaining the *Mycobacterium* single cell bacteria.

Wherein, in the foregoing method for preparing a tuberculosis vaccine, the resuspension medium in step c is phosphate buffer (PBST) with Tween. Further, the resuspension medium is PBS containing 0.05% to 0.1% Tween 80.

Further, the *Mycobacterium* single cell bacteria are BCG bacteria.

Preferably, for the preparation method according to claim 3, wherein the BCG bacteria are one or more of BCG Danish strain (Danish 1331), BCG Russian strain (Russian BCG-I), BCG Tokyo strain (Tokyo 172-1), and genetically engineered strains of the above-mentioned strains.

Further, for the preparation method according to claim 2, wherein after being irradiated by the irradiation at low dosage, uniformly and periodically, the *Mycobacterium* single cell bacteria have emissive filament-like structures on outer membrane, and the emissive filament-like structures surround the *Mycobacterium* single cell bacteria.

Wherein, in the preparation method for tuberculosis vaccine, concentration of the *Mycobacterium* single cell bacteria in the step c is $10^6$/mL to $10^8$/mL.

Further, concentration of the *Mycobacterium* single cell bacteria is $10^6$/mL to $10^{10}$/mL.

Wherein, in the preparation method for vaccine, the radiation is X-ray, γ-ray or radiation generated by the isotope radiation source $Co^{60}$.

Wherein, in the preparation method for tuberculosis vaccine, total dosage of the irradiation is equal to or greater than 4600 Gy (grays).

Further, total dosage of the irradiation is approximately: 3000 Gy, 3100 Gy, 3200 Gy, 3300 Gy, 3400 Gy, 3500 Gy, 3600 Gy, 3700 Gy, 3800 Gy, 3900 Gy, 4000 Gy, 4100 Gy, 4200 Gy, 4300 Gy, 4400 Gy, 4500 Gy, 4600 Gy, 4700 Gy, 4800 Gy, 4900 Gy, 5000 Gy, 5100 Gy, 5200 Gy, 5300 Gy, 5400 Gy, 5500 Gy, 5600 Gy, 5700 Gy, 5800 Gy, 5900 Gy or 6000 Gy.

Further, dosage rate of the irradiation is 10-100 Gy/min, (ii) the total dosage of the irradiation is equal to or greater than 4600 Gy, and (iii) the irradiation is performed periodically multiple times, with a time interval between every two irradiations.

Wherein, in the preparation method for tuberculosis vaccine, the specific operation mode of uniform and cyclic irradiation is as follows: the dosage rate is 10 to 20 Gy/min, the duration of each irradiation is 20 min with a time interval of 5 to 10 min, and the uniform irradiation is performed 8 to 10 times. Further, the uniform irradiation means that the dosage rate of irradiation is constant.

Wherein, in the preparation method for tuberculosis vaccine, the uniformity ratio of the irradiation dosage is ≤1.6.

Wherein, in the preparation method for tuberculosis vaccine, wherein when X-rays are used for the irradiation, energy of the X-ray ranges from 40 to 160 KVP and peak energy is 70 to 90 KVP.

Wherein, in the preparation method for tuberculosis vaccine, in order to remove the culture medium and corresponding bacterial extracellular secretions, the method further comprises a step of purifying the *Mycobacterium* single cell bacteria before and/or after taking the step of irradiation.

Further, a solvent that does not cause allergic reactions is used in the step of purification. The preferred solvent is PBS containing 0.05% to 0.1% Tween 80.

The present invention further provides a tuberculosis vaccine prepared by the foregoing method.

Further, the vaccine further comprises an adjuvant.

Wherein, the dosage form of the vaccine is a subcutaneous injection preparation, an intramuscular injection preparation, an oral or nasal inhalation preparation and other commonly used preparations.

In addition, the present invention further provides the use of the tuberculosis vaccine in the preparation of a medicament for preventing or treating infectious diseases caused by *Mycobacterium tuberculosis*.

Further, in the above use, the infectious diseases comprise at least one of pulmonary tuberculosis, meningeal tuberculosis, female pelvic tuberculosis, bone tuberculosis or intestinal tuberculosis.

Further, the tuberculosis vaccine can be used in synergy with first-line chemotherapeutic agents for the treatment of tuberculosis. The first-line chemotherapeutic agents for the treatment of tuberculosis include but are not limited to isoniazid, rifampicin, and streptomycin.

Further, the tuberculosis vaccine exerts immune protection effect by increasing the level of IL-12 and IFN-γ secreted by lymphocytes.

The tuberculosis vaccine in the present invention can be used for children, adolescents, adults, and immunocompromised populations, including HIV patients with *Mycobacterium tuberculosis* infection.

BENEFICIAL EFFECTS OF THE PRESENT INVENTION

The present invention provides a mycobacterial whole-cell vaccine treated by irradiation. By repeatedly stimulating bacteria using low dosage cyclical radiation, a better immunogenicity is obtained, to serve the purpose of inactivation and synergy. The present invention completely retains all the antigen characteristics of the bacteria, and can more rapidly stimulate stronger specific immune responses, thereby achieving effective and long-lasting immunity. The vaccine prepared using the present invention is an inactivated whole-cell vaccine, which has low toxicity, is rapid-acting and safer, and can be used for the prevention and treatment of tuberculosis for people having immunodeficiency. In addition, since the present invention can be applied to people having immunodeficiency, there is no need to distinguish different groups during vaccination, which will simplify the vaccination process and reduce the work of hospitals and health centers.

DETAILED DESCRIPTION OF THE EMBODIMENTS

Figure 1:
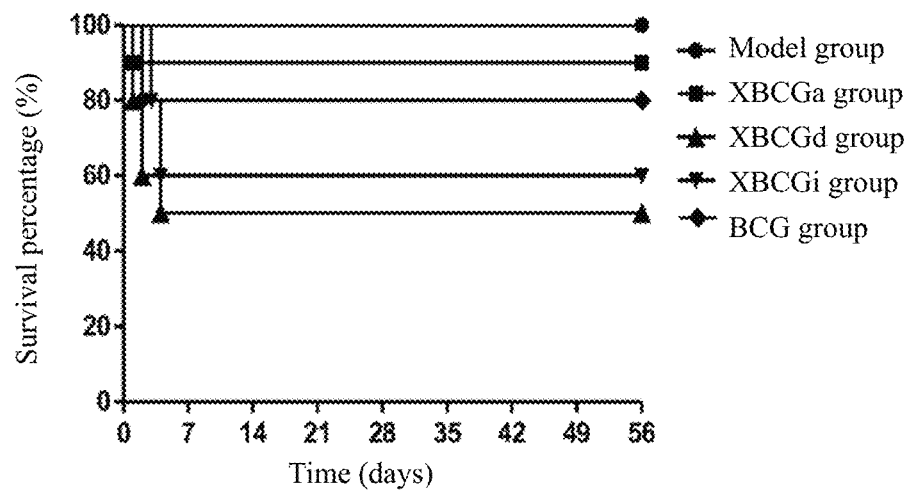
FIG. 1 showed the survival curves of mice immunized with TB vaccines with different irradiation methods with XBCGa representing a group of mice treated with uniform irradiation; constant dosage rate of 19 Gy/min, 20 min each time, 9 times in total, total dosage of irradiation of 3420 Gy, XBCGd representing a group of mice treated with decreasing irradiation, dosage rate decreased from 35 Gy/min to 19 Gy/min and 12 Gy/min, irradiation three times for each dosage rate, 20 min each time, 9 times in total, total dosage of irradiation of 3960 Gy, and XBCGi representing a group of mice treated with increasing irradiation, dosage rate increased from 12 Gy/min to 19 Gy/min and 35 Gy/min, irradiation three times for each dosage rate, 20 min each time, 9 times in total, total dosage of irradiation of 3960 Gy herein.

Embodiments given herein are to describe the present invention, but the content of the present invention is not limited to the embodiments. Therefore, the non-essential improvements and adjustments to the embodiments made by those skilled in the art according to the foregoing invention content still belong to the scope of protection of the present invention.

Unless otherwise specified, the terms "comprise(s)" and "include(s)" and their grammatical variations are used to indicate "open style" or "inclusive", so that they include the listed technical features but are also allowed to include other technical features that are not listed.

As used in the description, the term "approximately" (for example, total dosage of irradiation), is typically expressed as +1-5% of the value, and more typically as +/−4% of the value, and more typically as +/−3% of the value, more typically +/−2% of the value, even more typically +/−1% of the value, and still even more typically +1-0.5% of the value.

In this description, some embodiments may be disclosed in a format within a certain range. It should be understood that this description of "in a certain range" is only for convenience and brevity, and should not be construed as a rigid limitation to the disclosed range. Therefore, the description of the range should be considered as having specifically disclosed all possible subranges and independent numerical values within this range. For example, the description of the range 1-6 should be regarded as having specifically disclosed sub-ranges, such as, from 1 to 3, from 1 to 4, from 1 to 5, from 2 to 4, from 2 to 6, from 3 to 6, etc., and individual numbers within this range, such as 1, 2, 3, 4, 5, and 6. Regardless of the breadth of the range, the above rules apply.

The present invention provides a tuberculosis vaccine.

The vaccine is composed of mycobacterial whole-cells that have been irradiated. The radiation will cause the bacteria to lose their proliferation ability, but the structure is still intact, retaining most of the immunogenicity. The body can produce strong and effective immune responses to the immunogenic stimulations, that is, sufficient body fluid and cellular immunity to prevent and treat infections caused by *Mycobacterium tuberculosis*, while having adequate safety.

The present invention provides a method for preparing a tuberculosis vaccine, comprising the following steps:

first obtaining *Mycobacterium* single cell bacteria, and using low dosage radiation to irradiate uniformly and periodically the *Mycobacterium* single cell bacteria, to prepare the tuberculosis vaccine.

Before taking the step of irradiation, the method further comprises the following steps:
a. obtaining *Mycobacterium* strains,
b. inoculating and culturing to the logarithm growth phase,
c. adding resuspension medium, homogenizing, and sieving, and
d. obtaining the *Mycobacterium* single cell bacteria.

Wherein, the *Mycobacterium* single cell bacteria are BCG bacteria; the BCG bacteria are one or more of BCG Danish strain, BCG Russian strain, BCG Tokyo strain, and genetically engineered strains of the above-mentioned strains.

Wherein, after irradiating uniformly and periodically at low dosage radiation, the BCG bacteria have emissive filament-like structures on the outer membrane, and the emissive filament-like structures surround the BCG bacteria.

Wherein, in the foregoing method for preparing a tuberculosis vaccine, the resuspension medium in step c is phosphate buffer (PBST) with Tween. Further, the resuspension medium is PBS containing 0.05% to 0.1% Tween 80.

Wherein, in the foregoing method for preparing a tuberculosis vaccine, the concentration of the *Mycobacterium* single cell bacteria in step c is $10^6$/mL to 10/mL.

Wherein, the concentration of the *Mycobacterium* single cell bacteria is $10^6$/mL to $10^{10}$/mL.

Wherein, in the foregoing method for preparing a tuberculosis vaccine, the radiation is X-ray, γ-ray or radiation generated by the isotope radiation source $Co^{60}$.

Wherein, in the foregoing method for preparing a tuberculosis vaccine, the total dosage of irradiation is equal to or greater than 4600 Gy.

Wherein, the total dosage of irradiation is approximately: 3000 Gy, 3100 Gy, 3200 Gy, 3300 Gy, 3400 Gy, 3500 Gy, 3600 Gy, 3700 Gy, 3800 Gy, 3900 Gy, 4000 Gy, 4100 Gy, 4200 Gy, 4300 Gy, 4400 Gy, 4500 Gy, 4600 Gy, 4700 Gy, 4800 Gy, 4900 Gy, 5000 Gy, 5100 Gy, 5200 Gy, 5300 Gy, 5400 Gy, 5500 Gy, 5600 Gy, 5700 Gy, 5800 Gy, 5900 Gy or 6000 Gy.

Wherein, in the foregoing method for preparing a tuberculosis vaccine, (i) the dosage rate of irradiation is 10-100 Gy/min, (ii) the total dosage of irradiation is equal to or greater than 4600 Gy, and (iii) the cyclical irradiation is performed multiple times, with a time interval between twice irradiations.

Wherein, the dosage rate is 10 to 20 Gy/min, the duration of each irradiation is 20 min with a time interval of 5 to 10 min, and the cyclic irradiation is performed 8 to 10 times.

Wherein, in the foregoing method for preparing a tuberculosis vaccine, the irradiation can be carried out continuously in the process of cyclic irradiation, that is, after one irradiation ends, another round of irradiation starts immediately to start the cycle. In other words, the time interval between every twice irradiations can be set to zero.

Wherein, in the foregoing method for preparing a tuberculosis vaccine, the uniformity ratio of the irradiation dosage is ≤1.6.

Wherein, in the foregoing method for preparing a tuberculosis vaccine, the X-ray energy ranges from 40 to 160 KVP (peak kilovoltage) and the peak energy is 70 to 90 KVP when X-rays are used for the irradiation.

Wherein, the method further comprises a step of purifying the *Mycobacterium* single cell bacteria before and/or after taking the step of irradiation.

Wherein, a solvent that does not cause allergic reactions is used in the purification step.

The specific method for preparing the tuberculosis vaccine of the present invention is as follows:

(1) Obtaining mycobacterial bacterial strains; this bacterial strain includes but is not limited to clinical sample strains, commercial strains, and laboratory modified strains;

(2) Propagating bacteria: inoculating the bacterial strain obtained in step (1) in a suitable liquid medium to culture, allowing the bacteria in the logarithm growth phase; the medium, culture time, culture temperature and other conditions can be conventional conditions used in the art. The culture medium is suitable for bacterial proliferation, for example, the medium used in the examples; the culture condition is generally 35 to 37° C., preferably 37° C., and the preferred culture time is 3 weeks;

(3) Preparing single cell bacteria suspension: Collecting the bacteria in the logarithm growth phase obtained in step (2), adding the resuspension medium, homogenizing in a homogenizer, and sieving to obtain the bacteria suspension; the cell concentration in the bacterial suspension is $10^6$/mL to $10^{10}$/mL;

Wherein the concentration of *Mycobacterium* single cell bacteria is $10^6$/mL to $10^8$/mL;

(4) Purifying bacteria: Centrifuging the bacterial suspension again to collect the centrifugal precipitate. Repeating this step at least 2 times to ensure that all the centrifugal precipitates are bacteria, without culture medium and corresponding bacterial secretions, to reduce the allergic reactions of vaccine recipients;

(5) Irradiation: Resuspending the centrifugal precipitates after the purification treatment and transferring them to a non-metallic container, and uniformly and periodically irradiating the bacterial suspension using low dosage radiation for a long time. The dosage is 10 to 20 Gy/min, the duration of each irradiation is 20 min with a time interval of 5 to 10 min, and the uniform irradiation is performed 8 to 10 times, and the total dosage is 3000 Gy to 6000 Gy;

(6) Semi-finished product inspection: Inspecting the bacterial proliferation capacity and metabolic activity;

(7) Freeze-drying: subpackaging and freeze-drying the bacterial suspension obtained in step (5), to obtain a preventive and therapeutic tuberculosis vaccine;

(8) Vaccine storage: Storing the bacterial vaccine obtained in step (7) for standby use, preferably at −20° C. or −80° C.;

(9) Finished product inspection: detecting the content uniformity, conducting identification test, endotoxin and pure bacteria inspection, testing efficacy of the bacterial vaccine obtained in step (7) according to the third part of the Pharmacopoeia of the People's Republic of China.

When bacteria enrichment is performed in the invention, the count of bacteria is measured as needed to confirm the progress of culture. The number of bacterial cells can be reflected by absorbance OD (optical density) or turbidity, or can be determined using PCR DNA copy number, or other commonly used methods in the art.

After bacterial culture of the present invention, the collected bacterial cells should be purified. Various solvents that do not cause allergic reactions in the body can be used for washing in the purification step. The preferred solution is PBST washing. The bacteria collection and purification steps may also adopt the methods commonly used in the art such as concentration and column collection, etc. The purification step can be carried out before or after irradiation, or carried out both before and after irradiation.

In the present invention, the irradiation can be performed using X-rays, γ-rays, or isotope radiation source $Co^{60}$ rays, or other radiation sources commonly used in the art.

The total dosage of irradiation received by the bacteria shall meet the following requirements: the bacteria have no proliferation ability after irradiation treatment. The method for detecting whether the treated bacterial cells have the proliferation ability may be a commonly used method in the art.

Preferably, the following method is used: Take out the irradiated bacteria and dilute them with sterile normal saline, then spread them evenly on TH10 agar plates with a bacterial spreader, cultivate them in a 37° C. incubator for 3 weeks. Observe that there is no bacterial colony produced, that is, it is determined that the bacteria have no proliferation ability.

The present invention further provides a tuberculosis vaccine prepared by the above method, which may contain commonly used immune adjuvants, to enhance the immune effect of the vaccines.

The tuberculosis vaccine preparation provided herein may have multiple immunization methods, such as subcutaneous injection, intramuscular injection, oral administration, nasal inhalation, etc., or a combination thereof.

The tuberculosis vaccine preparation provided herein is a one-time immunization, but the specific implementation process is not limited thereto. The number of immunizations and the immunization time point can be changed or adjusted according to the actual situation.

The dosage of the tuberculosis vaccine preparation provided herein can be adjusted according to the condition of the recipient, and the preferred dosage is $(1\sim5)\times10^6$ bacterial cells each time. The specific number of immunizations can be adjusted according to the recipient's conditions.

The vaccines provided herein can be used to prepare medicines for preventing or treating diseases. For normal animals or humans, the vaccines prepared by the method of the present invention can enhance the body's ability to prevent and resist diseases, to achieve the goal of disease prevention. For animals and humans suffering from corresponding diseases or infections, especially adults with low immunity or who have infected with *Mycobacterium tuberculosis* previously, including HIV patients with *Mycobacterium tuberculosis* infection, this vaccine can induce the body to produce specific responses to pathogenic factors, to effectively eliminate pathogens, and achieve the purpose of treating diseases of patients.

Wherein, the tuberculosis vaccine can be used in synergy with first-line chemotherapeutic agents for the treatment of tuberculosis. The first-line chemotherapeutic agents for the treatment of tuberculosis include but are not limited to isoniazid, rifampicin, and streptomycin.

Wherein, the tuberculosis vaccine exerts immune protection effect by increasing the level of IL-12 and IFN-γ secreted by lymphocytes.

The present invention will be further described in combination with the specific examples, but it does not mean that the protection scope of the present invention is limited to the scope of the examples.

The mycobacterial strains described in the examples were all from The National Institute for Control of pharmaceutical and Biological Products. TH10 was purchased from Sigma-Aldrich (Shanghai) Trading Co., Ltd., and C57BL/6 mice and SCID mice were purchased from Beijing Huafukang Biotechnology Co., Ltd. The X-ray irradiator was a product of Rad Source, USA, model: RS 2000 (RS2000-Biological Irradiator). The remaining reagents and equipment were conventional products available on the markets.

Embodiment 1 Exploration of Inactivation Dose

Figure 14:
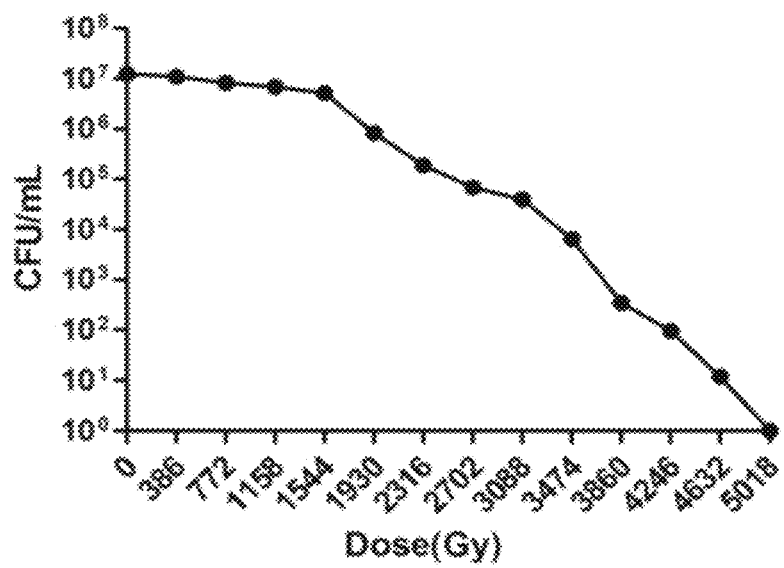
FIG. 14 showed exploration of inactivation dosage.

X-rays were used to inactivate live BCG bacteria. The relationship between the injection volume (CFU/mL) and the total dosage of irradiation was shown in FIG. 14. The inactivation effect was better when the total dosage of irradiation was 3K-6K.

Embodiment 2 Screening of Irradiation Methods for Tuberculosis Vaccines

C57BL/6 mice were selected and divided into model group (PBS), XBCGa group (uniform irradiation; constant dosage rate of 19 Gy/min, 20 min each time, 9 times in total, total dosage of irradiation of 3420 Gy), XBCGd group (decreasing irradiation, dosage rate decreased from 35 Gy/min to 19 Gy/min and 12 Gy/min, irradiation three times for each dosage rate, 20 min each time, 9 times in total, total dosage of irradiation of 3960 Gy), XBCGi group (increasing irradiation; dosage rate increased from 12 Gy/min to 19 Gy/min and 35 Gy/min, irradiation three times for each dosage rate, 20 min each time, 9 times in total, total dosage of irradiation of 3960 Gy), BCG group (BCG, commercially available), 10 animals each group, each animal was subcutaneously immunized once, with injection volume of 0.1 mL (about $10^6$ CFU/mL). After 4 weeks of immunization, the mice were challenged intravenously with freshly cultured BCG at a dosage of $10^7$ CFU. The survival of the mice was observed 8 weeks after challenge.

The results were shown in FIG. 1.

Except for the model group, animals in other immunization groups died within 1 week. Among them, the survival rate of animals in the BCG group was 80% and the death rate was 20%; the survival rate of animals in the XBCGa group was 90% and the death rate was 10%; the survival rate of animals in the XBCGd group was 50% and the death rate was 50%; and the survival rate of animals in the XBCGi group was 60% and the death rate was 40%.

The experimental results showed that, after mice were immunized with the tuberculosis vaccine (XBCGa) prepared by uniform irradiation, it was safer when their body was attacked by *Mycobacterium tuberculosis* again.

Embodiment 3 Observation on the Immune Protection of the Tuberculosis Vaccine in Different Irradiation Ways C57BL/6 mice were selected and divided into model group (PBS), XBCGa group (uniform irradiation), XBCGd group (decreasing irradiation), XBCGi group (increasing irradiation), BCG group, 10 mice in each group. Animals were subcutaneously immunized once, with injection volume of 0.1 mL (about $10^5$ CFU). After 4 weeks of immunization, the mice were challenged intravenously with freshly cultured BCG at a dosage of $10^6$ CFU. The spleen tissue homogenate was collected for 7H10 counting at the fourth week after challenge.

Figure 2:
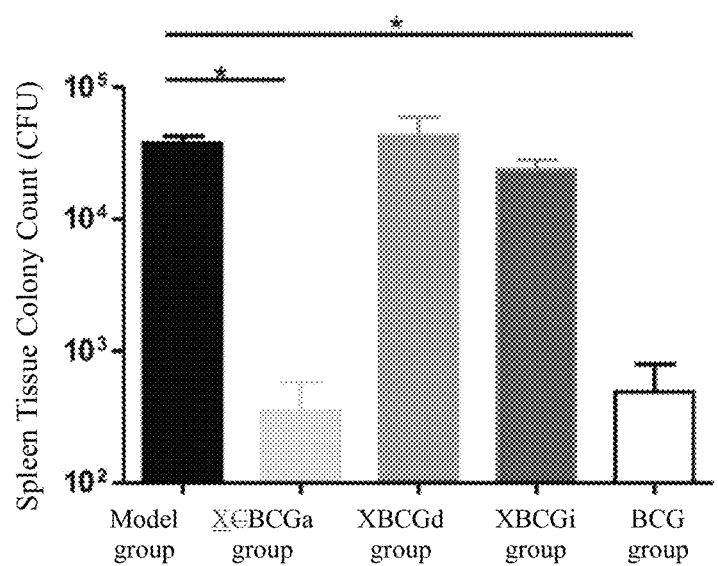
FIG. 2 showed TB vaccines with different irradiation methods, as described in the brief description with respect to FIG. 1, reduce the count of colony-forming units (CFU) in the spleen tissue of mice after challenge.

Results were shown in FIG. 2 and Table 1.

The experimental results showed that, in the Week 4, the CFU in the XBCGa group and the BCG group was decreased significantly compared with the model group, while that in the XBCGd group and XBCGi group had no significant change compared with the model group. The results indicated that, the tuberculosis vaccines (XBCGa) prepared by uniform irradiation had a better protective effect than those prepared by decreasing or increasing irradiation.

TABLE 1

| Group | Colony count of spleen tissues (CFU) |
| --- | --- |
| Model group | 37656 ± 10700 |
| XBCGa group | 349 ± 526 |
| XBCGd group | 42558 ± 37303 |
| XBCGi group | 23825 ± 9933 |
| BCG group | 490 ± 686 |

Embodiment 4 Preparation Method of Tuberculosis Vaccines

BCG strain D2BP302S11 was take, and cultured and proliferated in a modified Sauton medium (components: L-aspartic acid 4.00 g, citric acid 2.00 g, $K_2HPO_4$ 0.50 g, $MgSO_4$ 0.50 g, ferric citrate 0.05 g, 35 mL of glycerol, 2 mL of Tween 80, and 900 mL of distilled water) at 37° C. for 2 to 3 weeks. The bacterial biofilm was collected in a centrifuge tube, centrifuged at 3000 g (4120 rpm) for 10 min to remove the supernatant, appropriate amount of saline or PBS was added for resuspension, and then centrifuged at 3000 g (4120 rpm) for 10 min to remove the supernatant, then appropriate amount of PBST was added for resuspension, homogenized with a homogenizer, and then the bacterial solution was adjusted to $1 \times 10^7$ CFU/mL. The bacterial suspension was added into a 50 mL BD tube and irradiated in the radiation source center of the X-ray irradiator. The irradiation condition: 160 KV, 25 mA, layer 5, dosage rate of 19 Gy/min, 20 min each time at a time interval of 5 to 10 min, a total of 9 times of irradiation (about 4.5 h), a total dosage of irradiation of about 3.4 KGy.

Figure 3:
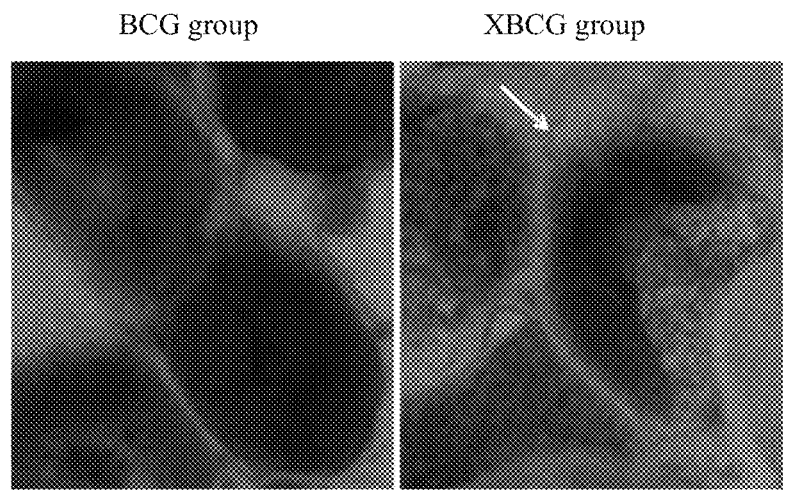
FIG. 3 showed the morphology of the bacterial cells under the transmission electron microscope, XBCG representing irradiated BCG herein.

The irradiated bacterial suspension and the unirradiated bacterial suspension were observed under SEM, to observe the changes in cell morphology. The results showed that, compared with the unirradiated bacterial cells, the bacterial cells of this vaccine (XBCG) remained intact, and the outer membrane density was reduced, and radiating filamentous structures appeared (shown by the arrow) to surround the bacterial cells. The changes in the distribution and density of bacterial contents indicated the changes of the structure and integrity of nucleic acids (FIG. 3).

0.1 mL of the irradiated bacteria were evenly spread onto a TH10 agar plate with a bacterial spreader, and incubated at 37° C. for 3 weeks. No growth of colonies was observed, indicating that the bacteria had no proliferation ability.

The bacterial suspension was subpackaged, and preserved at −20° C. for later use after freeze-drying.

In order to verify the efficacy of the present invention (i.e., tuberculosis vaccine) against diseases caused by *Mycobacterium tuberculosis* (including, but not limited to, tuberculosis, meningeal tuberculosis, female pelvic tuberculosis, bone tuberculosis or intestinal tuberculosis), the blood type infection mouse tuberculosis models were used to perform the following efficacy verification experiments in the present invention.

Figure 4:
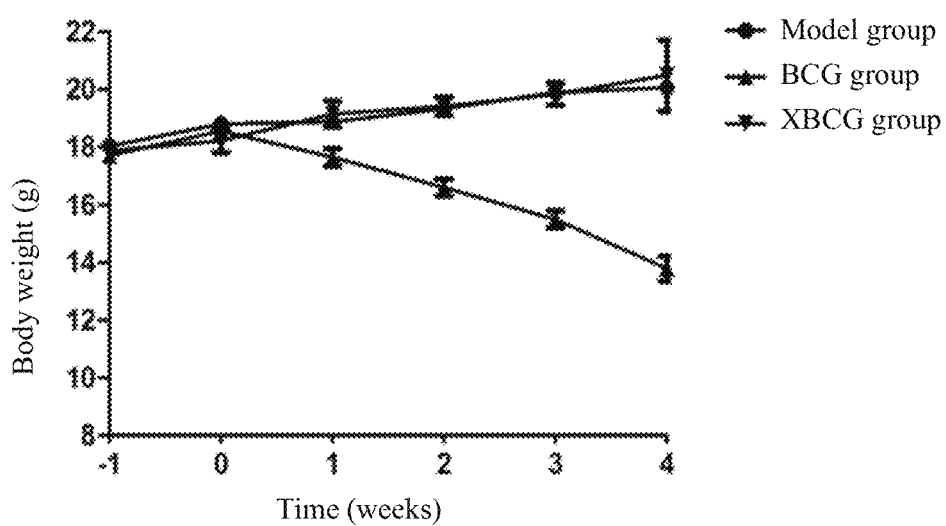
FIG. 4 showed the body weights of mice after immune challenge, XBCG representing irradiated BCG herein.
Figure 5:
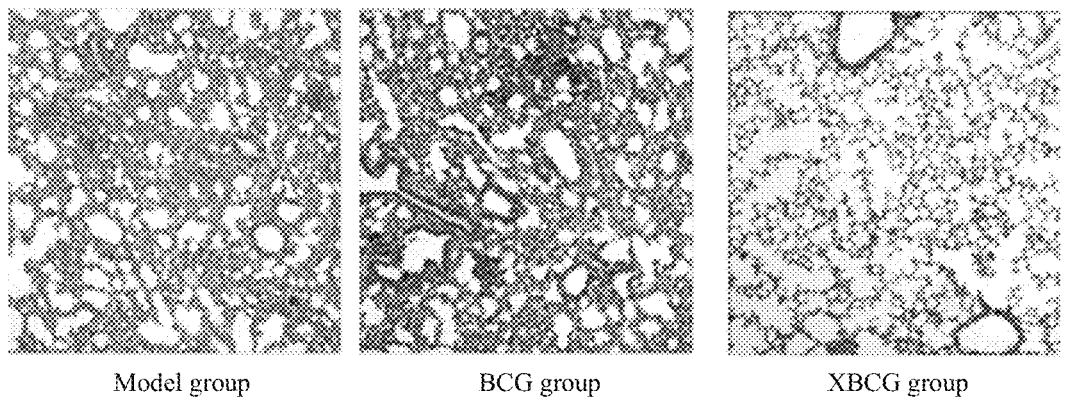
FIG. 5 showed the pathology of lung tissues of mice in 4 weeks after immune challenge, XBCG representing irradiated BCG herein.

Embodiment 5 Efficacy Verification 1 of Tuberculosis Vaccine of the Present Invention C57BL/6 mice were subcutaneously immunized and divided into vaccine (XBCG) immunization group, BCG group and model group, with 10 mice in each group. The mice in the experimental group were immunized with 0.1 mL (approximately $10^6$ CFU/mL) tuberculosis vaccine (XBCG) and BCG vaccine under the armpits, and the mice in the model group were immunized with 0.1 mL sterile PBS under the armpits to observe the survival status of mice. One week later, $2 \times 10^6$ live BCG bacteria were injected via the tail veins into the mice to challenge. FIG. 4 showed the results of body weights. Results showed that, the mice in the vaccine (XBCG) immunized group had a slowly increased body weight, without significant difference from the model group, while the body weight of mice in the BCG group was decreased continuously within 4 weeks after the live bacterial challenge, which was significantly different from the other two groups, suggesting that XBCG had smaller side effects and better safety. FIG. 5 showed the pathological examination of the lung tissues of mice in each group after 4 weeks. The results showed that the animals in the model group had thickened alveolar septum, dilated blood vessels in the lungs, and large amount of lymphocyte infiltration in and around the alveolar cavity. The BCG group showed no improvement. In the XBCG group, there was no thickening of alveolar septum and no lymphocyte infiltration.

Figure 6:
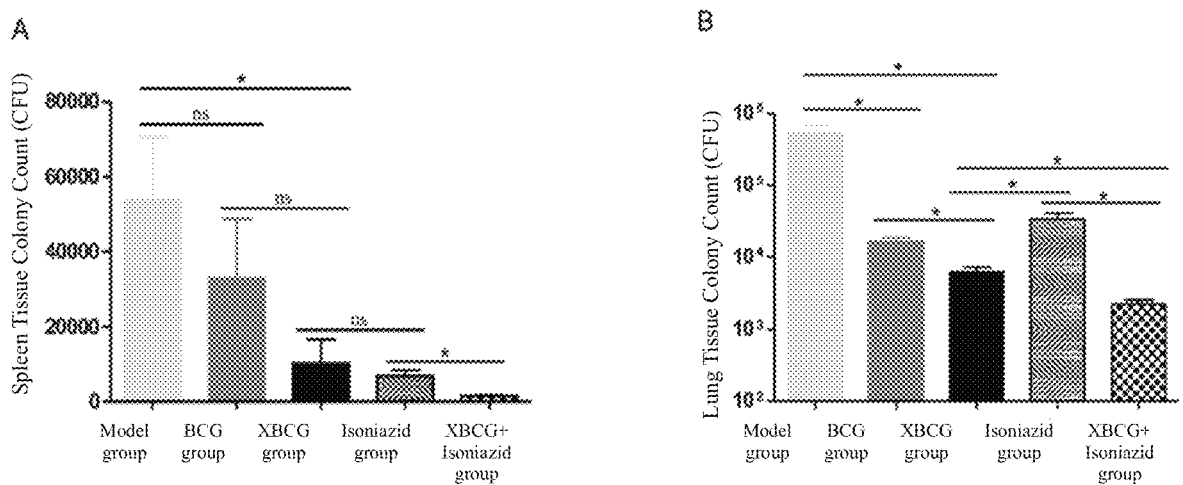
FIG. 6 showed the CFU count of spleen and lung tissues of mice 4 weeks after immune challenge; A represented CFU count of spleen tissue, B represented CFU count of lung tissues, XBCG representing irradiated BCG herein.

Embodiment 6 Efficacy Verification 2 of Tuberculosis Vaccine of the Present Invention C57BL/6 mice were subcutaneously immunized and divided into vaccine (XBCG) immunization group, isoniazid (INH) group, XBCG+INH group, BCG group and model group, 10 mice in each group. Mice in the experimental group were immunized with 0.1 mL (approximately $10^6$ CFU/mL) tuberculosis vaccines (XBCG) and BCG vaccines under the armpits. In the XBCG+INH group, in addition to subcutaneous immunization with XBCG, isoniazid was administered by gavage, while only isoniazid was administered by gavage in the isoniazid group. Mice in the model group were immunized with 0.1 mL of sterile PBS under the armpits, to observe the survival status of mice. One week later, $2 \times 10^6$ live BCG bacteria were injected into the mice to challenge. At the week 4, the mouse spleen and lung tissues were homogenized, and after 10-fold serial dilution with normal saline, 0.1 mL was taken and spread onto 7H10 plates, incubated at 37° C. for 3 weeks, and then CFU was counted. Results were shown in FIG. 6 and Table 2. The results showed that the bacterial load of the spleen and lungs in the XBCG group was significantly lower than that in the BCG group, suggesting that the vaccines of the present invention combined with the first-line chemotherapeutic agents may have a synergistic effect for the treatment of tuberculosis (in this example, isoniazid was studied and showed a synergistic effect. Therefore, it was inferred that the first-line anti-tuberculosis drugs such as rifampicin and streptomycin may also have a synergistic effect).

TABLE 2

| Group | Colony count of spleen tissues (CFU) | Colony count of lung tissues (CFU) |
| --- | --- | --- |
| Model group | 53628 ± 29301 | 530000 ± 293087 |
| BCG group | 32843 ± 27521 | 16667 ± 3786 |
| XBCG group | 10216 ± 12667 | 6333 ± 1701 |
| Isoniazid group | 6733 ± 2969 | 34000 ± 13115 |
| XBCG-isoniazid group | 1467 ± 611 | 2267 ± 611 |

Figure 7:
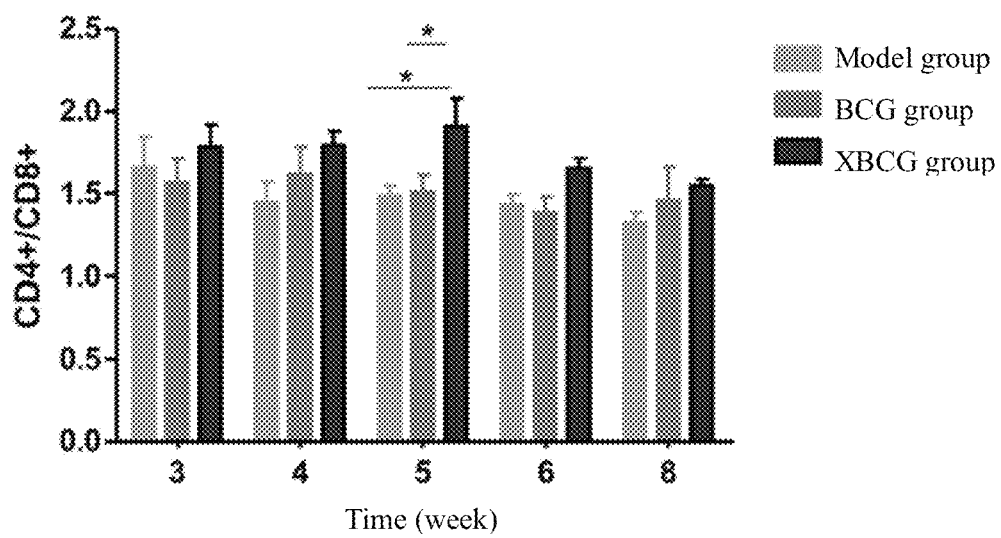
FIG. 7 showed splenic lymphocyte CD4+/CD8+ in 3 to 8 weeks after immunization, XBCG representing irradiated BCG herein.
Figure 8:
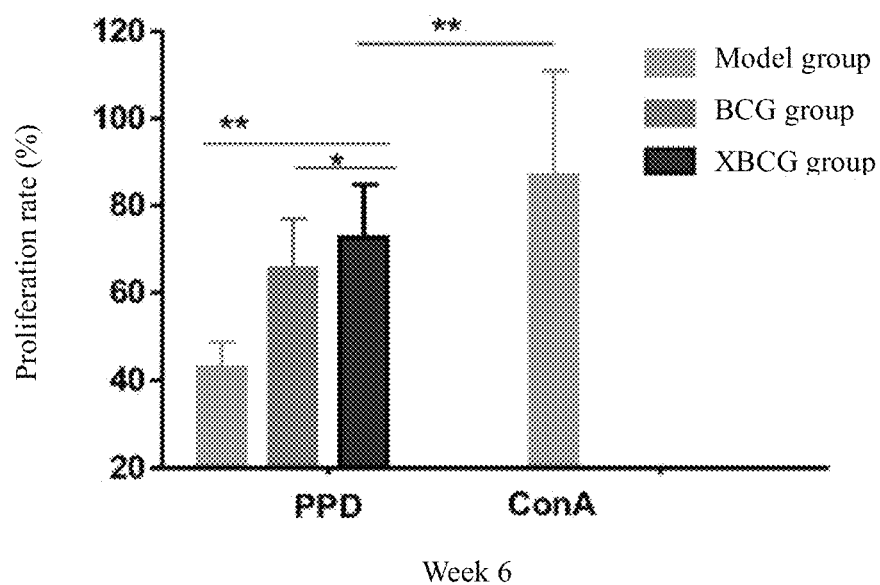
FIG. 8 showed that proliferation rate of splenic lymphocytes in 6 weeks after immunization, XBCG representing irradiated BCG herein.

Embodiment 7 Efficacy Verification 3 of Tuberculosis Vaccine of the Present Invention C57BL/6 mice were subcutaneously immunized and divided into vaccine (XBCG) immunization group, BCG group and model group, 24 mice in each group. Mice in the experimental group were immunized with 0.1 mL (approximately $10^6$ CFU/mL) tuberculosis vaccines (XBCG) and BCG vaccines under the armpits. Mice in the model group were immunized with 0.1 mL of PBS under the armpits, to observe the survival status of mice. At Weeks 1, 2, 3, 4, 5, 6, and 8 after immunization, mice were sacrificed by cervical dislocation method, the spleen was taken aseptically and ground, and the lymphocytes were separated with the mouse spleen cell separating medium, and the ratio of CD3+, CD4+, CD8+ cells were detected by a flow cytometer. The cells were inoculated into a 96-well plate and stimulated with tuberculin PPD or ConA. After cultured at 37° C. and 5% CO2 in a full humid condition for 72 hours, CCK8 (Cell Counting Kit 8) assay was performed to detect the cell proliferation. The experimental results were shown in FIG. 7 and FIG. 8. FIG. 7 and Table 3 showed that, in all groups, the ratio of CD4+/CD8+ of spleen lymphocytes of mice in XBCG group was higher than that in the BCG group and control group from week 3 to week 8, indicating that cellular immunity was enhanced. FIG. 8 and Table 4 showed that, for the proliferation rate of splenic lymphocytes under the stimulation of PPD or ConA, in the XBCG group, the spleen lymphocytes of mice at Week 6 had a higher cell proliferation rate than that of the BCG group and the model group under the stimulation of PPD, suggesting that the specific cellular immunity was stronger in the XBCG group.

TABLE 3

| | CD4+/CD8+ after immunization | | | | |
| --- | --- | --- | --- | --- | --- |
| Group | Week 3 | Week 4 | Week 5 | Week 6 | Week 8 |
| Model group | 1.66 ± 0.32 | 1.45 ± 0.22 | 1.49 ± 0.11 | 1.43 ± 0.11 | 1.33 ± 0.10 |
| BCG group | 1.57 ± 0.25 | 1.62 ± 0.30 | 1.51 ± 0.17 | 1.39 ± 0.17 | 1.46 ± 0.35 |
| XBCG group | 1.79 ± 0.23 | 1.79 ± 0.15 | 1.91 ± 0.29 | 1.65 ± 0.10 | 1.54 ± 0.07 |

TABLE 4

| | Splenocyte proliferation rate (%) | |
| --- | --- | --- |
| Group | PPD stimulation | ConA stimulation |
| Model group | 43.0 ± 10.0 | 87.1 ± 41.4 |
| BCG group | 65.7 ± 19.6 | — |
| XBCG group | 72.8 ± 20.9 | — |

Embodiment 8 Safety Test of Tuberculosis Vaccine

SCID mice were selected and divided into XBCG group, BCG group and PBS group, 8 mice in each group. The mice were immunized with 0.1 mL (approximately $10^7$ CFU/mL) tuberculosis vaccine (XBCG), BCG and PBS under armpits every day for 28 consecutive days, to observe the survival status of the mice. It should be noted that, in the above efficacy experiments, BCG and XBCG were for single immunizations, with an immunization dose of $10^6$ CFU each time. In the safety experiment, $10^7$ CFU per immunization was multiplied by the number of days for 28 days, i.e. it exceeded 100 times of the effective dose cumulatively.

Figure 9:
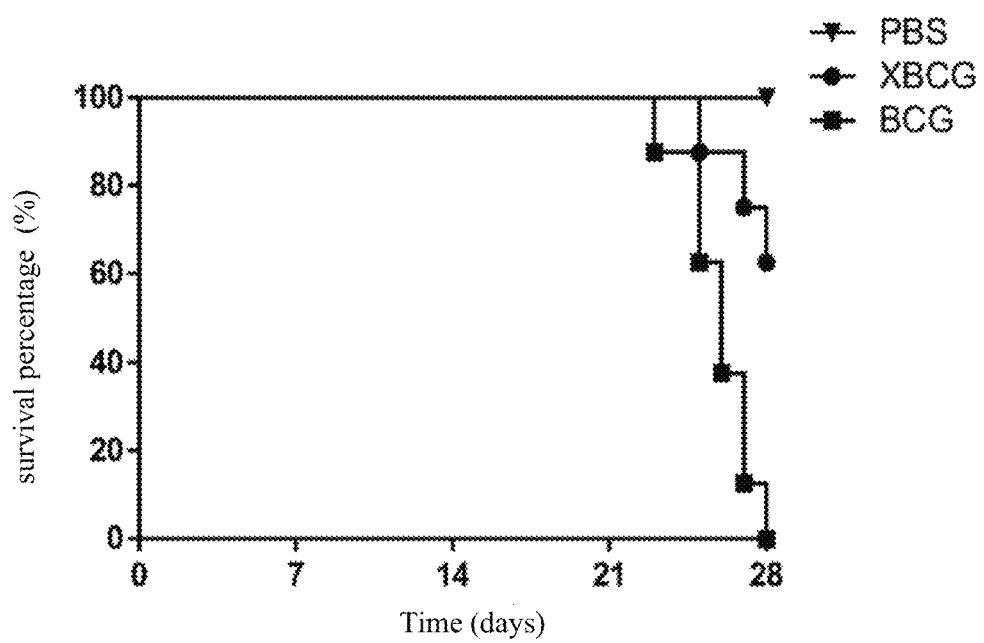
FIG. 9 showed the survival curve of SCID mice after cumulative immunization, XBCG representing irradiated BCG herein.

Except for the PBS group, the weight of the mice continued to decrease. Animals in the BCG group died from Day 23 and all died in Day 28, with a survival rate of 0. Animals in the XBCG group died from Day 25, and only 3 died until Day 28, with a survival rate of 62.5% (FIG. 9). Experimental results suggested that XBCG was safer than BCG.

Embodiment 9 Specific Immune Response of Mice

C57BL/6 mice were subcutaneously immunized and divided into vaccine (XBCG) immunization group, BCG group and model group, 6 mice in each group. Mice in the experimental group were immunized with 0.1 mL (approximately $10^6$ CFU/mL) tuberculosis vaccine (XBCG) and BCG under the armpits, and the mice in the model group were immunized with 0.1 mL PBS under the armpit. One week and two weeks after immunization, TB-PPD (10 g/20 mL) injected into the footpads to challenge. The thickness of the mouse footpads was measured before challenge, and 24 h after challenge, the thickness of the footpad at the attacked site was measured again, and the thickness of foot swelling and the mean value were calculated.

Figure 10:
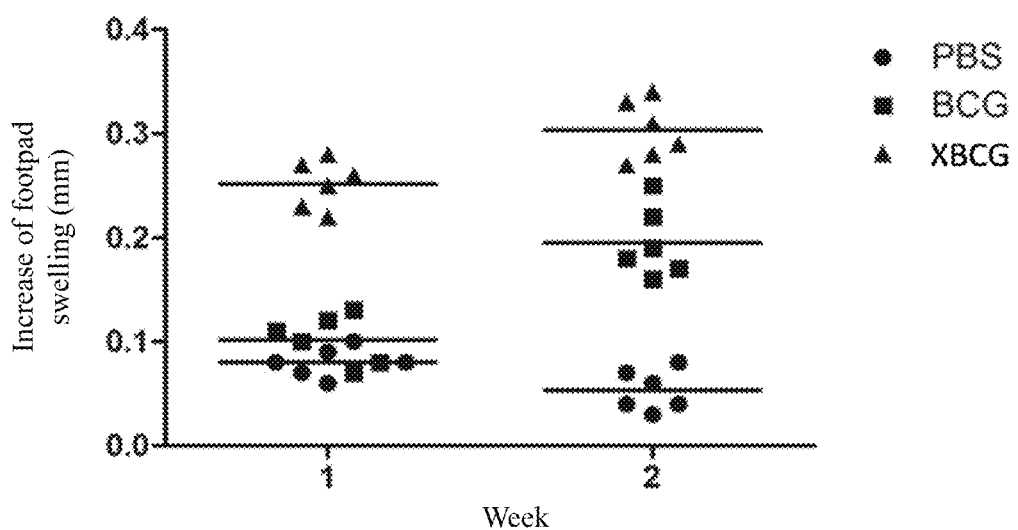
FIG. 10 showed specific immune response of mice, XBCG representing irradiated BCG herein.

Results: As shown in FIG. 10 and Table 5, mice were induced to produce cellular immunity in the XBCG group one week after immunization, which was faster than that in the BCG group and had a stronger immune effect.

TABLE 5

| Group | Increase of footpad swelling (mm) | |
|---|---|---|
| | 1 week after immunization | 2 weeks after immunization |
| PBS group | 0.08 ± 0.01 | 0.05 ± 0.02 |
| BCG group | 0.10 ± 0.02 | 0.20 ± 0.03 |
| XBCG group | 0.25 ± 0.02 | 0.30 ± 0.03 |

Embodiment 10 Effect on Cytokine Production of Mouse T Lymphocytes

Figure 11:
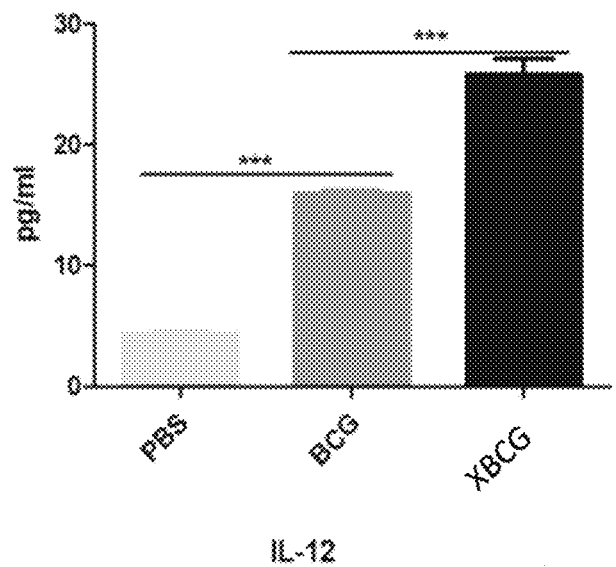
FIG. 11 showed the detection of IL-12 in mouse T lymphocytes, XBCG representing irradiated BCG herein.
Figure 12:
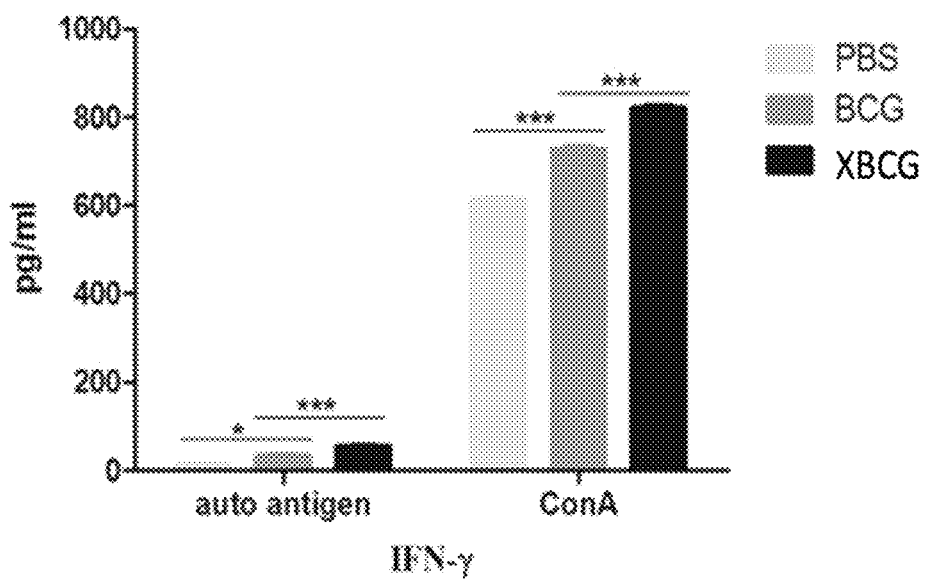
FIG. 12 showed the detection of IFN-γ in mouse T lymphocytes, XBCG representing irradiated BCG herein.

One week after the mice were immunized with this vaccine, the spleen was aseptically removed, the splenic lymphocytes were separated, and then the cytokines were stimulated and tested in vitro. Results were shown in FIGS. 11 and 12 and Tables 6 and 7 (FIG. 4 in the project material). The results indicated that the levels of IL-12 and IFN-γ secreted by splenic lymphocytes of mice in XBCG group were significantly higher than those in BCG group and control group.

TABLE 6

| Group | IL-12(pg/mL) |
|---|---|
| Model group | 4.4 ± 0.4 |
| BCG group | 15.9 ± 0.6 |
| XBCG group | 25.8 ± 2.9 |

Embodiment 11 Cell Immunity Promoted by Vaccines

1. The primary macrophages were collected in the mouse abdominal cavity, and BCG and X-ray-treated BCG (i.e. XBCG) were added to co-incubate them for 24 hours, to observe the number of bacteria in the macrophages and the survival of the macrophages. The trypan blue staining showed that, most of the macrophages treated with BCG survived; while most of the macrophages treated with XBCG died (data not shown).

2. Acid-fast staining showed that, when BCG acted on macrophages for 24 hours, the erosion of BCG into macrophages was observed under the microscope. It was noted that, when the live BCG entered the body of macrophages, macrophages were not activated. As a result, BCG could hide in the macrophages to escape the damage of immune responses. XBCG could enter macrophages, but the macrophages died, indicating that XBCG could allow macrophages to recognize its existence and activate the phagocytosis of macrophages.

Figure 13:
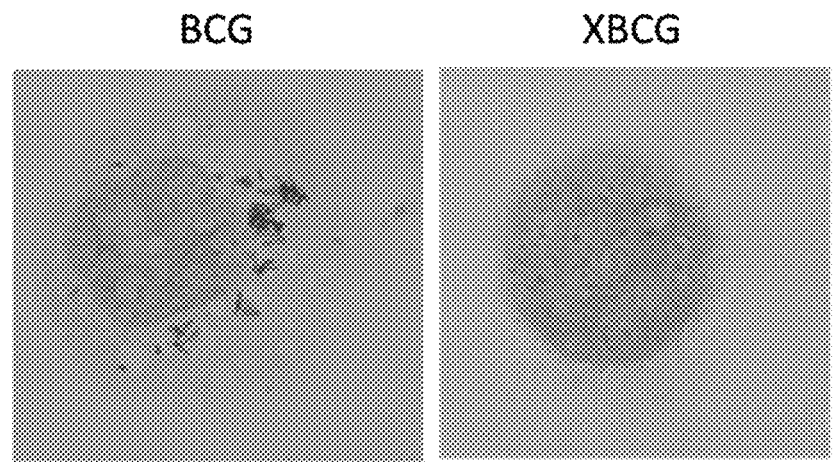
FIG. 13 showed the clearance of *Mycobacterium tuberculosis* by macrophages after vaccine stimulation, XBCG representing irradiated BCG herein.

As shown in FIG. 13, the left drawing showed the microscopic observation of removing *Mycobacterium tuberculosis* by macrophages in the BCG group. The macrophages were surrounded by *Mycobacterium tuberculosis*. It could be found that macrophages in the BCG group could not eliminate all *Mycobacterium tuberculosis*. In the right drawing, macrophages in the XBCG group could eliminate all *Mycobacterium tuberculosis*, indicating that the XBCG group can more effectively stimulate the immune clearance of macrophages against bacteria.

According to the above experimental results, the present invention provides a tuberculosis vaccine. It is an inactivated whole-full vaccine, which has low toxicity, is rapid-acting and safer, and capable of producing enough antibodies and cellular immune molecules against potential infectious bacteria, so it can be used for the prevention and treatment of tuberculosis for people having immunodeficiency, providing a new option for preventing or treating tuberculosis.

Finally, it should be noted that the foregoing embodiments are only used to illustrate the technical solutions of the present invention and not to limit them. Although the present invention has been described in detail with reference to the preferred embodiments, those of ordinary skill in the art should understand that the technical solutions of the present invention may be modified or substituted equivalently without departing from the purpose and scope of the technical solutions of the present invention, and all of which should fall into the scope of claims of the present invention.

The invention claimed is:

1. A preparation method for tuberculosis vaccine, comprising the following steps:
   First obtaining *Mycobacterium* single cell bacteria, and using radiation to irradiate uniformly the *Mycobacterium* single cell bacteria, to prepare the tuberculosis vaccine;
   Wherein the radiation is X-ray, γ-ray or radiation generated by isotope radiation source Co60, the *Mycobacterium* single cell bacteria are Bacille Calmette-Guerin (BCG) bacteria;
   Wherein dosage rate of the irradiation is 10-20 Gy/min, and the irradiation is performed multiple times, with a time interval between every two irradiations;
   Wherein duration of each irradiation is 20 min with the time interval of 5 to 10 min, and the irradiation is performed 8 to 10 times, wherein before taking the step of irradiation, said method further comprises the following steps:
   a. obtaining *Mycobacterium* strains,
   b. inoculating and culturing to logarithmic growth phase,
   c. adding resuspension medium, homogenizing, and sieving, and
   d. obtaining the *Mycobacterium* single cell bacteria.

2. The preparation method according to claim 1, wherein the BCG bacteria are one or more of BCG Danish 1331 strain, BCG Russian BCG-1 strain, and BCG Tokyo 172-1 strain.

3. The preparation method for tuberculosis vaccine according to claim 1, wherein concentration of the *Mycobacterium* single cell bacteria is $10^6$/mL to $10^8$/mL.

4. The preparation method for tuberculosis vaccine according to claim 1, wherein total dosage of the irradiation is approximately: 3000 Gy, 3100 Gy, 3200 Gy, 3300 Gy, 3400 Gy, 3500 Gy, 3600 Gy, 3700 Gy, 3800 Gy, 3900 Gy, 4000 Gy, 4100 Gy, 4200 Gy, 4300 Gy, 4400 Gy, 4500 Gy, 4600 Gy, 4700 Gy, 4800 Gy, 4900 Gy, 5000 Gy, 5100 Gy, 5200 Gy, 5300 Gy, 5400 Gy, 5500 Gy, 5600 Gy, 5700 Gy, 5800 Gy, 5900 Gy or 6000 Gy.

5. The preparation method for tuberculosis vaccine according to claim 1, wherein uniformity ratio of dosage of the irradiation is ≤1.6.

6. The preparation method for preparing tuberculosis vaccine according to claim 1, wherein, when X-rays are used for the irradiation, energy of the X-ray ranges from 40 to 160 KVP and peak energy is 70 to 90 KVP.

7. The preparation method for tuberculosis vaccine according to claim 1, further comprising a step of purifying the *Mycobacterium* single cell bacteria before and/or after the step of irradiation.

8. A tuberculosis vaccine prepared by the method of claim 1.

9. The tuberculosis vaccine according to claim 8, wherein the vaccine further comprises an adjuvant.

10. The preparation method according to claim 1, wherein after being irradiated, the BCG bacteria have emissive filament-like structures on outer membrane, and the emissive filament-like structures surround the BCG bacteria.

11. The preparation method for tuberculosis vaccine according to claim 1, wherein the resuspension medium in step c is phosphate buffer PBST with Tween.

12. The preparation method for tuberculosis vaccine according to claim 1, wherein concentration of the *Mycobacterium* single cell bacteria is $10^6$/mL to $10^{10}$/mL.

13. The preparation method for tuberculosis vaccine according to claim 7, wherein a solvent that does not cause allergic reactions is used in the step of purification.

\* \* \* \* \*